United States Patent [19]

Furillo

[11] Patent Number: 4,978,353
[45] Date of Patent: Dec. 18, 1990

[54] METHOD AND MEANS FOR PROTECTING CORNEAL ENDOTHELIUM AND IRIS DURING IOL IMPLANTATION

[76] Inventor: Michael L. Furillo, 29310 Whitingham Ct., Agoura Hills, Calif. 91301

[21] Appl. No.: 411,719

[22] Filed: Sep. 25, 1989

[51] Int. Cl.⁵ ............................................... A61F 2/16
[52] U.S. Cl. ....................................................... 623/6
[58] Field of Search .......................... 623/6, 4; 606/107

[56] References Cited

U.S. PATENT DOCUMENTS 4,600,004  7/1986  Lopez et al. .......................... 623/6 X
4,638,056  1/1987  Callahan et al. ...................... 623/6 X

OTHER PUBLICATIONS

"Endothelial Damage from Interaocular Lens Insertion" by Herbert E. Kaufman & Jeffrey I. Katz, *Investigative Ophthalmology*, vol. 15, No. 12, Dec. 1976, pp. 996–1000.

*Ophth*, vol. 86, Feb. 1979, "Protection of Corneal Endothelium During Intraocular Lens Implantation Using Polymacon, a New Surgical Technique" by P. L. Levy et al., pp. 219–227.

*Primary Examiner*—Ronald Frinks
*Attorney, Agent, or Firm*—John J. Leavitt

[57] ABSTRACT

Presented is a method and a structure for protecting the corneal endothelium of the eye during the implantation procedure of an intraocular lens. The structure includes a hydrophilic material that is formed to envelop the anterior and posterior surfaces of an optic, the anterior and posterior portions of the structure being joined integrally by a connecting strap that spans a peripheral portion of the underlying or sandwiched optic to retain the covering material on the optic during the insertion process. The connecting strap may also be used to confine one of the haptics to the outer periphery of the optic during the insertion process, and may also be used as a tab to facilitate withdrawal of the protective device from the eye after implantation of the intraocular lens. The protective device shields the corneal endothelium and iris tissue from inadvertent harmful contact with the polymethylmethacrylate material from which a large proportion of intraocular lenses are fabricated.

22 Claims, 2 Drawing Sheets

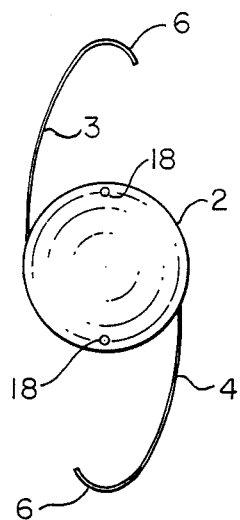
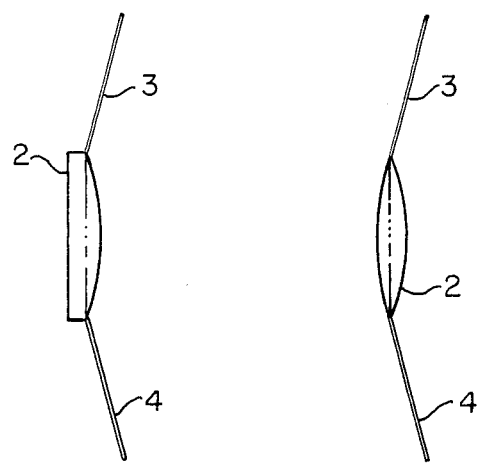
FIG. 1    FIG. 2    FIG. 3
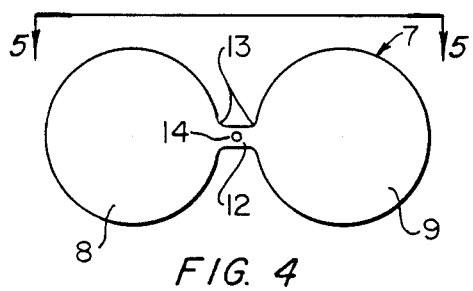
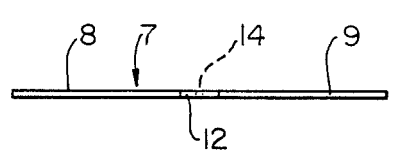
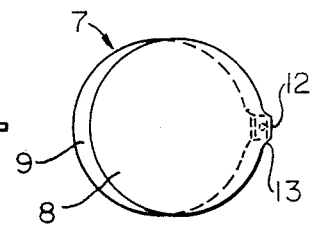
FIG. 4    FIG. 5    FIG. 6
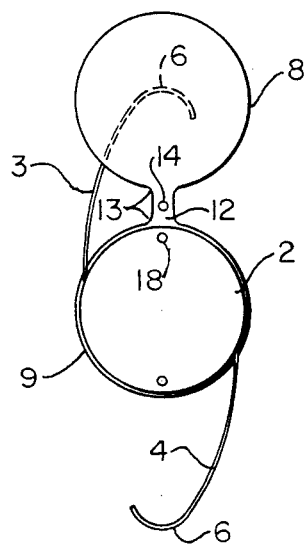
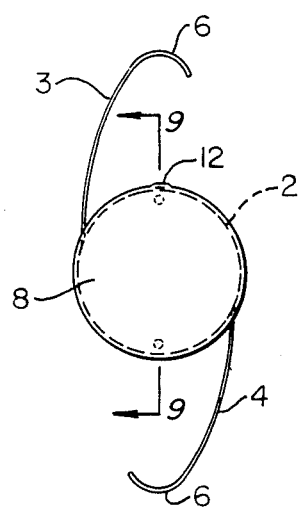
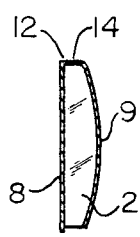
FIG. 7    FIG. 8    FIG. 9
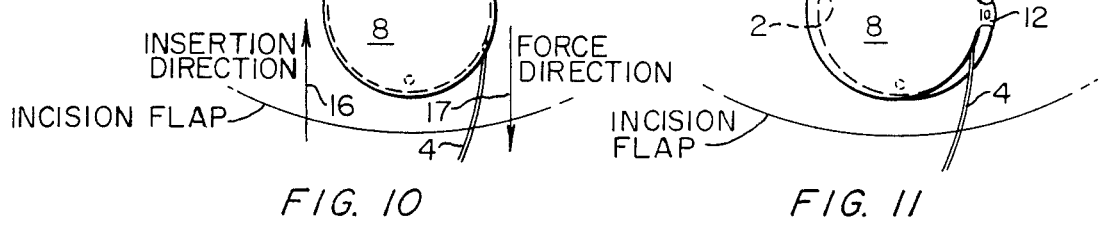
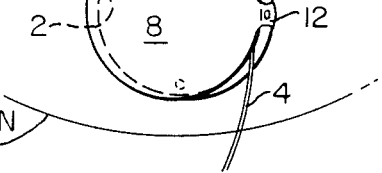
FIG. 10    FIG. 11

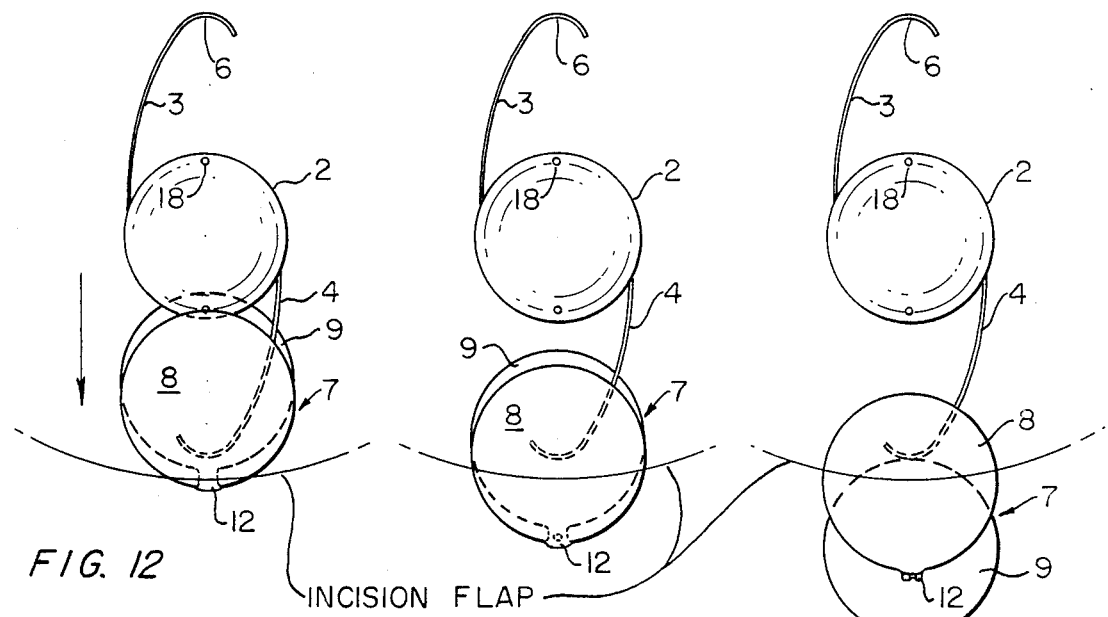
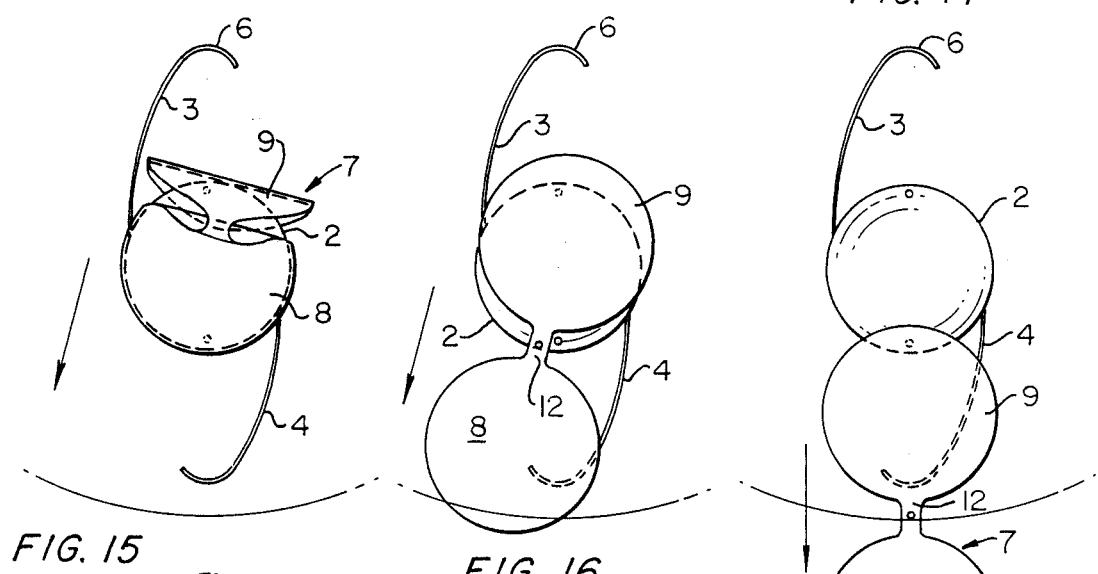
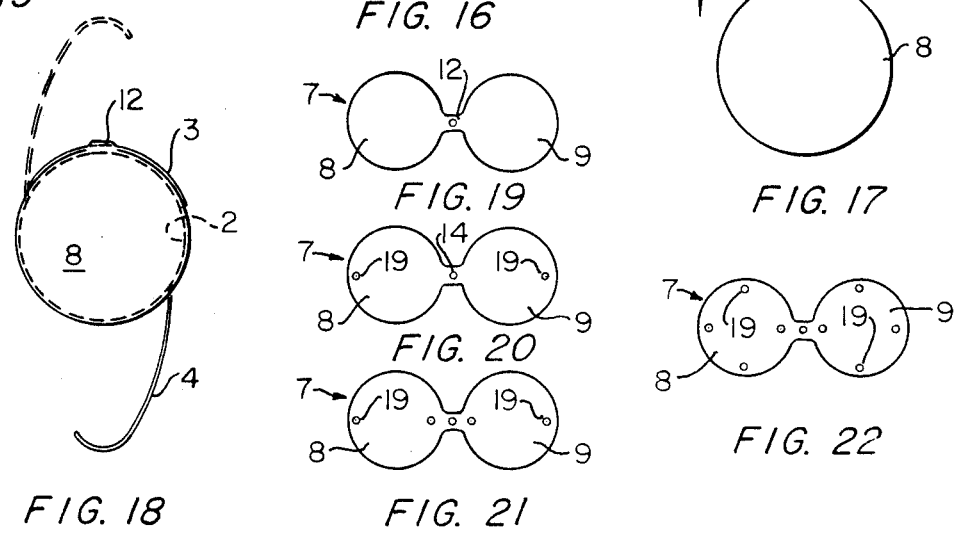

METHOD AND MEANS FOR PROTECTING CORNEAL ENDOTHELIUM AND IRIS DURING IOL IMPLANTATION

BACKGROUND OF THE INVENTION

1. Field of the Invention.

This invention relates to the procedure for the implantation of intraocular lenses, and particularly to a method and means for effecting such implantation procedure while minimizing the likelihood of damage to the corneal endothelium and iris.

2. Description of the Prior Art

A preliminary patentability and novelty search of the prior patent art pertaining to the instant invention has revealed the existence of the following U.S. Pat. Nos.:

| | | |
|---|---|---|
| 4,600,003 | 4,600,004 | 4,657,011 |
| 4,693,716 | 4,701,181 | 4,769,034 |

U.S. Pat. Nos. 4,600,003 and 4,600,004 relate to a tool for inserting an intraocular lens through an incision made for that purpose. The lens is loaded onto the tool, the tool is then inserted through the incision, and the lens is then pushed off the tool and into position within the eye. A major purpose of the tool is to retain the haptics in a collapsed condition during the insertion process. It is stated in these patents that the tool may be fabricated from any of the common plastics currently in use.

U.S. Pat. No. 4,657,011 relates to a guide device for assisting the insertion of an intraocular lens into the capsular bag from which the natural lens has been aspirated. The guide, as stated in the patent in column 3, lines 17 through 20, inclusive, is preferably made from a thin, flexible material which will not interact with the eye, for example, thin metal like stainless steel or plastic like polyethylene or polypropylene. One end of the strip, which has a distal end portion bent over upon the remainder of the strip, is first inserted into the eye through an appropriate incision, and then the lens to be implanted is caused to slide along the guide until it is deposited within the capsular bag. The guide is then withdrawn.

U.S. Pat. No. 4,693,716 relates to a multi-part lens structure and does not appear to have any relevance with respect to the instant invention.

U.S. Pat. No. 4,701,181 relates to a specific lens design rather than to a device for protecting the corneal endothelium or the iris tissue. The stated purpose of the design is to enable utilization of polymethylmethacrylate (PMMA) for the haptics in place of haptics formed from prolene (polypropylene) which are stated as subject to degradation in the eye. Thus, the lens structure disclosed by this patent includes a lens formed from PMMA and haptics formed from PMMA, a material that is particularly susceptible of causing damage to the corneal endothelium if the PMMA comes into contact with it. Nothing in this patent suggests a means of preventing such damaging contact of the lens or haptics with the corneal endothelium or the iris tissue.

Until relatively recent years, lenses were implanted in the anterior chamber of the eye, and surgical techniques were developed to facilitate insertion of the lenses and suspension of the lenses on the iris. Very early, it was recognized that PMMA (polymethylmethacrylate) was a desirable material for use as an optic because of its optical clarity and the ease with which it can be milled and lathed. As early as 1976 however it was revealed in an article by *Kaufman and Katz*, published in Invest Ophthalmol Visual Science, volume 15, pages 996–1000, that even a momentary contact of the PMMA lens surface and the corneal endothelium causes a physical adhesion of endothelium cells to the lens, the cells being torn from the endothelium when the surfaces are separated, causing extensive cell damage or cell death. An article by *Levy and Roth*, published in OPHTH, Vol. 86, pages 219–227, Feb. 1979 explains an experiment using cat eyes in which a new surgical technique is described which implements a sheet of Polymacon cut to the size of the anterior chamber and draped over the anterior surface of the lens so that during insertion the corneal endothelium is protected from contact with the intraocular lens. As stated in the article, a significant reduction in endothelium cell loss occurs when the corneal endothelium is protected against contact with the intraocular lens. Numerous other articles and experiments confirm this early finding. It is surprising therefore that more prior art references have not been found disclosing structural implementation of the corneal endothelium protection concept revealed in the scientific literature.

In another article entitled *Corneal Endothelium Loss With New Intraocular Lenses*, published in 1984 in the American Journal of Ophthalmology, volume 98, pages 137–165, there is described a comparison of the damage that results to the corneal endothelium by no contact (0.4%); by contact with uncoated methylmethacrylate (62%); by contact with hydrogel intraocular lenses (3.6%) which is said to be not significantly different from the "no contact" degree of damage; by contact with methylmethacrylate lenses coated with sodium hyaluronate (27.4%); and methylmethacrylate lenses coated with methylcellulose (57.2%).

This article goes on to discuss that of the approximately 600,000 patients (in 1984) who undergo cataract operations each year in the United States alone, about 70% of them receive an intraocular lens implant. It goes on to say that the most serious late complication of implant surgery is intractable corneal edema leading to loss of corneal transparency which may not appear until three to five years after implant. It attributes corneal decompensation largely to the result of profound loss of endothelial cells during surgery by contact of the methylmethacrylate lens with the corneal endothelium. Even after implantation, it is said that there is a progressive loss of endothelial cells which may be the result of chronic uveitis.

Recognition of the danger of touching the corneal endothelium is indicated by the fact that for about the last eight years, ophthalmologists have relied on viscoelastic gels that are injected into the anterior chamber of the eye to form a barrier tending to prevent inadvertent contact of the PMMA lens with the corneal endothelium. Such viscoelastic gels are costly, and pose the risk of postoperative complications such as increased intraocular pressure and inflammation. Because of these risks, many surgeons now aspirate the gel out of the eye prior to wound closure in an effort to minimize such risks.

In view of these findings, particularly since PMMA intraocular lenses appear to be the least costly and the type that are presently most prescribed and implanted, it is even more surprising that a greater effort has not been expended in conceiving and manufacturing protective devices, apart from injected gels, to be used by the surgeon during the implantation procedure. One justification that might be offered is that ophthalmologists are confident they can implant a lens without touching the corneal endothelium, and the use of a protective device constitutes an implied derogation of their ability. Nevertheless, in view of the severe and lasting damage that can occur by the mere touching of the corneal endothelium with the surface of the PMMA intraocular lens, it is submitted that the protective device forming the subject matter of the present invention is sorely needed and will find immediate acceptance by ophthalmologists.

Accordingly, one of the objects of the present invention is the provision of a method for protecting the corneal endothelium and/or iris tissue during the implantation procedure without unduly complicating the procedure, and perhaps even simplifying the procedure by eliminating some of the anxiety that a surgeon must experience in an effort to avoid contacting the corneal endothelium with the intraocular lens.

Another important object of the present invention is the provision of a protective device that may be applied to an intraocular lens prior to insertion into the eye for the purpose of forming a protective boundary between the lens structure and the corneal endothelium and/or the iris tissue.

Still another object of the invention is the provision of a protective device that is biocompatible with the corneal endothelium and which may be applied to the intraocular lens in such a manner that the insertion force applied to the lens acts to ensure that the protective device remains on the lens until it is properly positioned within the eye.

A still further object of the invention is the provision of a protective device for application to an intraocular lens, particularly a lens fabricated from PMMA, which is easily removed from the eye following insertion of the lens.

Still another object of the invention is the provision of a protective device that is fabricated from hydrophilic material and which may be applied to the lens so as to completely cover either the anterior surface thereof, the posterior surface thereof, or both anterior and posterior surfaces.

Yet another object of the invention is the provision of a protective device fabricated from hydrophilic material that contains sufficient water when applied to the lens that the protective device has a natural affinity for the lens, causing the hydrated protective device to adhere adequately to the lens so as to minimize inadvertent displacement of the protective device on the lens.

Still another object of the invention is the provision of a protective device for application to an intraocular lens which forms a temporary boundary between the lens body and surrounding tissue, but which nevertheless permits adjustment of the position of the lens body so as to enable alignment of the optic axis of the lens with the optic axis of the eye.

A still further object of the invention is the provision of a protective device for application to an intravocular lens according to the foregoing objects which is colored to provide visual differentiation from the intraocular lens to which it is applied.

The invention possesses other objects and features of advantage, some of which, with the foregoing, will be apparent from the following description and the drawings. It is to be understood however that the invention is not limited to the embodiment illustrated and described since it may be embodied in various forms within the scope of the appended claims.

SUMMARY OF THE INVENTION.

In terms of broad inclusion, one aspect of the invention relates to the method of enveloping an intraocular lens with a protective device that is fabricated from a material that is biocompatible with the corneal endothelium and/or iris tissue. In this aspect of the invention, the PMMA intraocular lens optic is covered by the protective device so that either one or both of the anterior and posterior surfaces of the lens optic are covered by the biocompatible material. The biocompatible protective covering is applied to the lens in hydrated condition, along with a small amount of balanced saline solution, and remains on the lens during the entire insertion and positioning procedure and is then withdrawn from the interior of the eye, leaving the intraocular lens properly positioned within the eye. During the insertion procedure care is of course taken to avoid contacting any part of the lens assembly with the corneal endothelium, but should it happen that the lens optic accidently contacts the corneal endothelium, little or no damage occurs because of the biocompatibility of the protective device material with the corneal endothelium and iris tissue.

In terms of structure, the protective device includes, but is not limited to, an anterior portion and a posterior portion that preferably correspond to the anterior and posterior surfaces, respectively, of the PMMA lens optic. The two portions of the device are connected by a separable or severable strap that extends between two adjacent peripheries of the anterior and posterior portions. The material from which the anterior and posterior portions are formed is preferably a hydrophilic material containing at least 30% by weight of water, as is the connecting strap. Because of the nature of the hydrophilic material, and its dimensions, the anterior and posterior portions, connected by the strap, form a unitary structure that may be sterilized and packed flat in dehydrated or hydrated condition. When hydrated, the hydrophilic strap forms a flexible hinge enabling re-arrangement of-the anterior and posterior portions from their initial relationship in a single plane to a parallel relationship in two parallel planes, and connected across the parallel planes by the hinge-like strap. Thus, when applied to the lens optic, the hinge-like strap abuts the edge of the lens optic so that when the lens is inserted through the incision, the hinge-like strap prevents inadvertent displacement of the protective device in relation to the enveloped lens optic. Following placement and positioning of the lens optic, the protective device may be rotated about the optical axis of the lens until the hinge-like strap is approximately opposite the incision, where the protective device may be withdrawn through the incision by tugging on the strap, causing the device to slide off the optic and out of the eye without dislodging the optic. In this respect, the injection of a small amount of balanced saline solution between the protective device and the lens facilitates movement of the protective device in relation to the lens optic. Additionally, the protective device may be formed from a material that is colored to aid in visually differentiating the protective device from the lens. Where desirable, the hinge-like strap may be severe and each of the now separated anterior and posterior portions may be removed individually through the incision, the balanced saline solution freeing the severed anterior and posterior portions to allow them to more freely slide over the lens optic when tugged.

BRIEF DESCRIPTION OF THE DRAWINGS

FIG. 1 is a plan view of a conventional PMMA intraocular lens including a haptic structure and an optic portion to which the protective device of the invention may be applied.

FIG. 2 is a side elevational view of the lens of FIG. 1, having a plano-convex optic portion.

FIG. 3 is a side elevational view similar to FIG. 2 but in which the optic portion possesses a biconvex configuration.

FIG. 4 is a plan view of the protective device of this invention shown extended prior to application on a lens.

FIG. 5 is an edge view of the protective device of FIG. 4 taken in the direction indicated by the arrows on line 5—5 in FIG. 4.

FIG. 6 is a perspective view of the protective device shown rearranged from the planar position of its parts in FIG. 4 to a superposed position of the flexibly interconnected anterior and posterior portions of the protective device.

FIG. 7 is a plan view similar to FIG. 4 but showing the protective device partially applied to a lens assembly.

FIG. 8 is a plan view showing the protective device fully applied to a lens assembly.

FIG. 9 is a sectional view taken in the plane indicated by the line 9—9 in FIG. 8.

FIG. 10 is a plan view of the fully assembled combination of intraocular lens and protective device shown in relation to the incision flap that gives access to the interior of the eye.

FIG. 11 is a view similar to FIG. 10, but showing the protective device rotated clockwise on the enveloped lens optic to bring the hinge-like interconnecting strap joining the anterior and posterior portions of the protective device closer to the incision flap for eventual withdrawal from the eye.

FIG. 12 is a plan view showing the protective device as a unitary member partially withdrawn through the incision flap.

FIG. 13 is a plan view similar to FIG. 12 showing the protective device fully disengaged from the lens optic and almost fully withdrawn from the eye.

FIG. 14 is a plan view showing the interconnecting strap severed to separate the anterior and posterior portions of the protective device, and showing both the anterior and posterior portions partially withdrawn through the incision, with the posterior portion withdrawn farther than the anterior portion.

FIG. 15 is a view illustrating another method of withdrawing the protective device from the eye after proper placement of the intraocular lens therein.

FIG. 16 is a view illustrating the continued withdrawal of the protective device as a whole as in FIG. 15 and showing the protective device almost free of the optic.

FIG. 17 is a view similar to FIGS. 15 and 16 showing the protective device as a whole free from the optic and almost totally withdrawn through the incision.

FIG. 18 is a plan view showing one of the haptic filaments caught beneath the hinge strap prior to insertion into the eye, to be released subsequent to insertion in the eye.

FIGS. 19 through 22 each illustrate the protective device of the invention in plan, with no apertures formed in the anterior and posterior portions in FIG. 19, and with varying patterns of apertures formed in the anterior and posterior portions of the protective device in the remaining views.

DESCRIPTION OF THE PREFERRED EMBODIMENTS

In terms of greater detail, the method that I have developed for protecting the corneal endothelium and/or iris tissue during implantation of an intraocular lens comprises the steps of enveloping selected portions of the lens assembly, particularly the optic, with a covering material that is biocompatible with the corneal endothelium so that even if contact is made between the optic and corneal endothelium no damage, or negligible damage, will occur. To this end, I have developed a structure or protective device from such biocompatible material that may be applied to the optic in such manner that the insertion force of implantation of the lens contributes to adherrence of the covering material to the lens, while facilitating withdrawal of the lens-covering protective device formed from biocompatible material when the implantation procedure has been completed. The method of the invention will become more apparent as it is described hereinafter in conjunction with the structural aspects of the protective device.

Referring to the drawings, particularly FIGS. 1 through 3, there is there shown a conventional type intraocular lens assembly comprising a lens body or optic 2 which may be of the plano-convex configuration illustrated in FIG. 2, or which may be of the biconvex configuration illustrated in FIG. 3. In either case, the protective device of the invention is adapted to envelop or cover either or both the anterior and posterior surfaces of the optic. The lens assembly also includes a haptic structure which in the lens illustrated comprises filamentary extensions 3 and 4 which extend generally in opposite directions from the optic, and each of which is provided at its distal end with a curved portion 6 that is adapted to contact tissue within the eye to support the lens body so that the optical axis of the lens body is aligned with the optical axis of the eye.

The protective device of the invention is shown in FIGS. 4, 5 and 6 apart from the intraocular lens, and shown in FIG. 4 in extended or planar form. As there shown, the protective device is designated generally by the numeral 7, and comprises an anterior portion 8 integrally interconnected with a posterior portion 9 by an intermediate strap 12 formed from the same material as the anterior and posterior portions. In this respect, I have found that a satisfactory material is a hydrophilic material that can be hydrated to absorb approximately 30% to 70% by weight of water. A suitable material is a hydrophilic material sold commercially under the trade name Polymacon which constitutes a 2-hydroxyethyl methyl methacrylate polymer cross-linked with ethylene glycol dimethacrylate. Other hydrophilic materials may also be used and some of these are listed in U.S. Pat. No. 4,787,904, included herein by reference, where they are disclosed and claimed for use in the fabrication of the optic of an intraocular lens assembly.

The protective device of the invention is preferably formed from hydrophilic material having a thickness that when hydrated is very flexible so that when either the anterior or posterior portions, or both, are draped on or applied to the corresponding surface or surfaces of the optic, the protective material conforms itself to the configuration of the optic, the wet planar surface of the anterior or posterior portions of the protective device clinging tenaciously to the corresponding surface of the optic to which it is applied. It should be noted in this respect that the hinge strap 12 projects integrally from adjacent peripheral edges of the anterior and posterior portions and is also hydrated at the time the remainder of the protective device is hydrated. However, because it may be expected that some tension will be applied to the hinge strap at the time the lens is inserted through the incision, the hinge strap 12, while being fabricated from the same hydrophilic material as the anterior and posterior portions which it joins, may be formed with additional thickness to increase its strength and resistance to elongation due to the application of tension in the manner indicated. Concomitantly, since it is desirable for the ophthalmologist to be able to sever the hinge strap easily, if that is in accord with the surgeon's technique for withdrawal of the protective device, the strap may be merged smoothly and integrally at its roots 13 with each of the portions 8 and 9, but intermediate its roots the strap is necked down to a lesser width as illustrated, and may be provided with a small aperture 14 that decreases the amount of material required to be severed by the surgeon.

As illustrated in FIG. 7, one method of application of the protective device to an intraocular lens is to deposit the intraocular lens assembly, and a drop or two of balanced saline solution, onto the hydrated surface of one of the portions 8 or 9, say the posterior portion 9. In this position, the posterior surface of the optic is in intimate contact with the wet surface of the posterior portion 9, and the opposite anterior portion 8 overlies the haptic 3, the end portion of which is shown in broken lines. The anterior portion 8 is then carefully displaced upwardly and over so as to lie against the anterior surface of the optic, with the hinge strap 12 flexing in the region of the aperture 14 to provide a tab that extends beyond the peripheries of both the anterior and posterior protective portions 8 and 9. It should be noted from FIGS. 7 and 8 that in this preferred embodiment, the outer peripheries of the protective portions 8 and 9 extend slightly beyond the outer periphery of the optic so as to completely envelope the optic with the hydrophilic protective covering formed by the anterior and posterior portions 8 and 9.

It will of course be understood that while FIG. 7 illustrates placement of the optic on the posterior portion of the protective device, with subsequent application of the anterior portion 8, several other techniques may be used to cause envelopment of the optic by the protective device. Thus, one such procedure might include appropriate support of the optic with its anterior surface facing upward, followed by placement of the hydrated anterior portion 8 on the anterior surface of the optic, with the posterior portion 9 being swung downwardly and around to adhere to the posterior surface of the optic. In this procedure, care is exercised that the hinge strap is properly oriented adjacent the root of one of the haptics, and the posterior portion is applied so that the haptic adjacent the hinge strap is left free to become the inferior haptic inserted into the eye. Again, the use of a small amount of a balanced saline solution aids application of the device.

Alternatively, this procedure may be altered slightly by conforming the haptic 3 associated adjacent the hinge strap to the circular configuration of the optic as shown in full lines in FIG. 18, and then folding the posterior portion down and around the conformed haptic so that the haptic lies caught in the bight formed by the folded hinge strap, which then retains the resilient haptic closely confined to the outer periphery of the optic, with the natural resilience of the haptic being resisted by the hinge strap. This procedure simplifies the insertion procedure because it controls the location of the inferior haptic in relation to the optic, leaving the surgeon free to concentrate on proper placement of the optic within the eye in a proper orientation. The surgeon may then simply clip the hinge strap to release the temporarily captive haptic, which now springs outwardly to cooperate with the opposite haptic to retain the optic properly aligned with the optical axis of the eye.

In the procedure wherein the inferior haptic is left free, i.e., not captive under the hinge strap, as shown in FIG. 10, the intraocular lens assembly is inserted through the incision in the direction indicated by the arrow 16. The hinge strap spans the leading peripheral edge of the optic as shown, so that any frictional force exerted on the surfaces of the covering protective portions 8 and 9 as the lens assembly is inserted exerts a force on the covering material in the direction of the arrow 17. This imposes a tensioning force, albeit small, on the hinge strap, which presses more tightly against the associated peripheral edge of the optic, thus preventing the frictional force applied on the hydrophilic covering portions to inadvertently displace the optic during the insertion procedure and the subsequent positioning of the optic for proper placement and alignment within the eye. Retention of the covering material on the optic during insertion is also aided by the pressure imposed by the forceps with which the optic is held by the surgeon.

After insertion and proper placement of the optic within the eye, it becomes necessary to remove the protective device from the optic and from the eye. As seen in FIG. 11, the tab formed by the folded hinge strap constitutes a means which may be grasped by forceps, a rotational force being applied thereto to rotate the protective device about the optic axis while the anterior and posterior protective covering portions 8 and 9 remain adherent on the respective surfaces of the optic. The injection of a small amount of a balanced saline solution facilitates this procedure. The protective device is rotated until the hinge strap tab is in approximately the position illustrated in FIG. 11, at which time the surgeon may decide to continue the rotation of the protective device until the tab achieves a position approximately diametrically opposed to the position shown in FIG. 10, at which time the surgeon may tug on the tab to effect downward displacement of the entire protective device as shown in FIG. 12. Application of continued withdrawal force effects extraction of the protective device through the incision as illustrated in FIG. 13.

Alternatively, when the surgeon has rotated the protective device to the position illustrated in FIG. 11, he may choose to sever the tab with an appropriate instrument so that the anterior and posterior portions 8 and 9 are separated from each other, i.e., no longer connected, the remnants of the tab attached to each of the anterior and posterior portions forming a means by which each separate portion 8 and 9 may be withdrawn through the incision as illustrated in FIG. 14. In this procedure, it is contemplated that the posterior portion 9 will be withdrawn first so as to retain the anterior portion between the iris and the optic and between the corneal endothelium and the optic during the withdrawal procedure of the posterior portion. When the posterior portion has been completely withdrawn, then the tab of the anterior portion may be easily grasped and the anterior portion withdrawn from the eye through the incision with little likelihood of the anterior portion 8 coming into contact with the corneal endothelium or the iris tissue. But even if it does, since the protective device is formed from a hydrophilic material that is biocompatible, little or no damage will occur to these members.

A third way in which the protective device may be removed is illustrated in FIGS. 15 through 17, inclusive. In this procedure, while the tab is in the position illustrated in FIG. 10, it is grasped by an appropriate instrument, such as a forcep, and a downward force is applied so that the posterior protective portion 9 is drawn over the top edge of the optic as shown in FIG. 15. The anterior portion 8, because of its soft quality due to hydration, and its flexibility due to its thinness, may fold or roll over upon itself or simply slide off the anterior surface of the optic, while the posterior portion slides down the anterior surface as the result of the continued application of tension on the tab applied in a downward direction. Continued downward displacement of the protective device will result in the device assuming the attitude illustrated in FIG. 16, where the device as a whole may be withdrawn through the incision as shown in FIG. 17.

To facilitate manipulation of the lens assembly during the implantation procedure, the optic may be provided with diametrically opposed apertures 18 near the outer periphery of the optic that enable the surgeon to insert an instrument to rotate the optic or to displace it laterally so as to align the axis of the optic with the optical axis of the eye. Some optics have no apertures, while others may have one or more apertures. In any event, in order that these apertures, where present, may still be used by the surgeon, the protective device may be provided with corresponding apertures 19 so that even when the protective device covers the optic, the aperture or apertures in the optic will be accessible to the surgeon through the apertures 19 in the anterior and posterior portions 8 and 9 of the protective device. Both portions 8 and 9 are provided with the access apertures so that the surgeon will not be required to match the anterior portion 8 of the protective device with the anterior surface of the optic, either anterior portion 8 or posterior portion 9 being similarly applicable to the optic. This construction of the protective device is shown in four different patterns in FIGS. 19 through 22, inclusive.

Having thus described the invention, what is believed to be new and novel and sought to be protected by letters patent of the United States is as follows.

I claim:

1. The method of protecting the corneal endothelium and/or iris of an eye during an intraocular lens implantation procedure, comprising the steps of:
    (a) causing the entire anterior and posterior surfaces of the intraocular lens to be covered prior to insertion into the eye by a material having juxtaposed portions of a preformed shape which is less susceptible to damaging the corneal endothelium and/or iris than the material from which the lens is formed;
    (b) causing the intraocular lens having said anterior and posterior surfaces covered to be inserted into the eye and positioned substantially in ultimate position therein, and
    (c) withdrawing the lens covering material from the eye in substantially said preformed shape while leaving the intraocular lens in implanted position within the eye.

2. The method according to claim 1, in which said lens covering material is applied in a manner to extend beyond the peripheral edge of the intraocular lens.

3. The method according to claim 1, in which said lens covering material is applied to said lens in an orientation with respect to the lens so that insertion forces applied to the lens during implantation are transferred to said lens covering material to retain said lens covering material on the lens.

4. The method according to claim 1, in which said intraocular lens and said covering material are oriented relative to each other in a first orientation during insertion into the eye and after insertion said covering material is re-oriented in relation to the lens to facilitate withdrawal of the covering material from the eye.

5. The method according to claim 1, in which said lens covering material disposed on said lens anterior and posterior surface portions are interconnected adjacent a peripheral portion of the lens.

6. The method according to claim 1, in which said lens covering material disposed on the anterior and posterior surface portions of the lens extends to at least the periphery of the lens to envelop said anterior and posterior surface portions, and selected corresponding edge portions of said anterior and posterior covering material portions are interconnected across the periphery of the lens.

7. The method according to claims 1, 2, 3, 4, 5 or 6 in which said lens covering material is formed from a hydrophilic material.

8. The method according to claim 1, in which said intraocular lens having said anterior and posterior portions covered is caused to be implanted in the posterior chamber of the eye.

9. A protective device for protecting the corneal endothelium and/or iris during implantation in the eye of an intraocular lens assembly including an intraocular lens portion having anterior and posterior surfaces defined by a peripheral edge, comprising:
    (a) a unitary member having juxtaposed portions adapted to be releasably applied to the anterior and posterior surfaces of the intraocular lens; and
    (b) means interconnecting said juxtaposed portions whereby said portions may selectively be disposed in a common plane or in parallel planes.

10. The protective device according to claim 9, in which said unitary member is fabricated from a hydrophilic material.

11. The protective device according to claim 9, in which said unitary member is fabricated from a material that is biocompatible with ocular tissue including at least said corneal endothelium and iris tissue.

12. The protective device according to claim 9, in which at least one of said juxtaposed portions substantially corresponds in size and shape to said anterior surface of the lens portion, and said means interconnecting said juxtaposed portions comprises an integral flexible tie joining selected edge portions of said juxtaposed portions.

13. The protective device according to claim 9, in which said unitary member is fabricated from a material that is biocompatible with ocular tissue, and said unitary member is colored to provide visual differentiation from the intraocular lens to which it is to be applied.

14. The protective device according to claim 9, in which said unitary member is fabricated from a hydrophilic material that possesses at least a 30% water content by weight.

15. The protective device according to claim 9, in which said means interconnecting said juxtaposed portions lies in said common plane when said juxtaposed portions lie in said common plane.

16. The protective device according to claim 9, in which said means interconnecting said juxtaposed portions lies in a plane perpendicular to the planes in which said juxtaposed portions lie when said juxtaposed portions of the unitary member are contained in parallel planes.

17. The protective device according to claim 9, in which at least one of said juxtaposed portions is provided with at lease one aperture whereby to give access through said aperture to an underlying intraocular lens.

18. The protective device according to claim 9, in which said means interconnecting said juxtaposed portions constitutes a strap-like severable tie integrally interconnecting associated edge portions of said juxtaposed portions, whereby when said strap-like tie is severed the remnants of said tie become opposed tabs extending beyond the outer periphery of the juxtaposed portions.

19. In combination with an intraocular lens assembly adapted to be surgically implanted in the human eye through an incision in the eye in close proximity to the corneal endothelium and the iris and including a lens portion having anterior and posterior surfaces defined by a peripheral edge and formed from a material incompatible with the corneal endothelium and iris tissue and a haptic for supporting the lens portion within the eye, a protective device mounted on said lens assembly, comprising:
  (a) a unitary member fabricated from material that is biocompatible with the corneal endothelium and iris tissue and releasably mounted on said intraocular lens whereby when said lens assembly with said unitary protective device mounted thereon is inserted into the eye through said incision said corneal endothelium and iris tissue ar shielded from said incompatible lens material by said protective device, said unitary member including:
    (1) an anterior portion removably applied on the anterior surface of the intraocular lens;
    (2) a posterior portion removably applied to the posterior surface of the intraocular lens; and
    (3) means interconnecting said anterior and posterior portions of the unitary member across the peripheral edge of the intraocular lens.

20. The method of protecting the corneal endothelium and/or iris of an eye during an intraocular lens implantation procedure, comprising the steps of:
  (a) causing selected portions of the intraocular lens to be covered prior to insertion into the eye by a material less susceptible to damaging the corneal endothelium and/or iris than the material from which the lens is formed;
  (b) causing the intraocular lens having said selected portions covered to be inserted into the eye and positioned substantially in ultimate position therein; and
  (c) withdrawing the lens covering material from the eye while leaving the intraocular lens in implanted position within the eye;
  (d) said lens covering material constituting a unitary structure including interconnected anterior and posterior portions when applied to the intraocular lens and during insertion of the lens into the eye, and divided into separate and unconnected anterior and posterior portions prior to withdrawal from the eye.

21. The method of protecting the corneal endothelium and/or iris of an eye during an intraocular lens implantation procedure, comprising the steps of:
  (a) causing selected portions of the intraocular lens to be covered prior to insertion into the eye by a material less susceptible to damaging the corneal endothelium and/or iris than the material from which the lens is formed;
  (b) causing the intraocular lens having said selected portions covered to be inserted into the eye and positioned substantially in ultimate position therein; and
  (c) withdrawing the lens covering material from the eye while leaving the intraocular lens in implanted position within the eye;
  (d) said lens covering material being applied to the anterior and posterior surface portions of the intraocular lens prior to insertion into the eye;
  (e) said lens covering material disposed on the anterior and posterior surface portions of the lens extending to at least the periphery of the lens to envelop said anterior and posterior surface portions, selected corresponding edge portions of said anterior and posterior covering material portions being interconnected across the periphery of the lens;
  (f) said selected corresponding edge portions of said covering material that extend across the periphery of the enveloped lens being oriented in relation to the lens diametrically opposite the periphery of the lens against which force is applied to effect insertion of the lens into the eye whereby application of said insertion force on the lens causes the interconnected peripheral edge portions of the covering material to impinge on the periphery of the lens opposite the periphery against which insertion force is applied, re-orienting the covering material on the lens after insertion into the eye so that the interconnected peripheral edge portion of the covering material lies adjacent the peripheral edge of the lens against which insertion force was applied during insertion of the lens, thereafter severing the interconnection between anterior and posterior portions of the covering material whereby said covering material is converted from a unitary state to divided and separate anterior and posterior portions, and then independently withdrawing from the eye said divided and separate anterior and posterior lens covering portions.

22. The method according to claims 20 and 21, in which said lens covering material is formed from a hydrophilic material.

* * * * *